(12) United States Patent
Anderson et al.

(10) Patent No.: US 6,325,766 B1
(45) Date of Patent: Dec. 4, 2001

(54) GUIDEWIRE HAVING SUBSTANTIALLY NICKEL-FREE HIGH-NITROGEN AUSTENITIC STAINLESS STEEL ALLOY

(75) Inventors: David Anderson; Marc Mehrzad Jalisi, both of Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/452,563

(22) Filed: Dec. 1, 1999

(51) Int. Cl.⁷ .............................. A61B 5/00; A61M 25/00
(52) U.S. Cl. ............................................................. 600/585
(58) Field of Search ........................ 600/585; 416/223 R

(56) References Cited

U.S. PATENT DOCUMENTS 5,769,796 * 6/1998 Palermo et al. .................... 600/585
5,879,132 * 3/1999 Usami et al. ...................... 416/223 R
5,916,166 * 6/1999 Reiss et al. ............................ 600/585

\* cited by examiner

*Primary Examiner*—John P. Lacyk
*Assistant Examiner*—Brian Szmal
(74) *Attorney, Agent, or Firm*—Fulwider Patton Lee & Utecht, LLP

(57) ABSTRACT

An improved guidewire having a core member formed from high-nitrogen nickel-free austenitic stainless steel alloy. This core member exhibits high tensile strength coupled with high ductility and high fatigue strength. The invention may also comprise a shapeable member for a guidewire formed from high-nitrogen nickel-free austenitic stainless steel alloy. The high-nitrogen nickel-free austenitic stainless steel alloys comprise less than about 0.3 weight % nickel and about 1 weight % nitrogen.

12 Claims, 1 Drawing Sheet

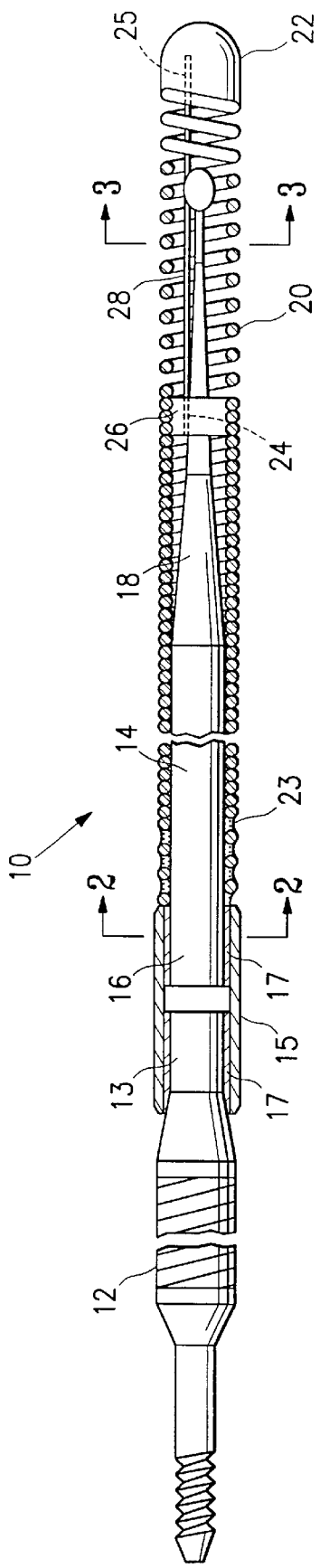
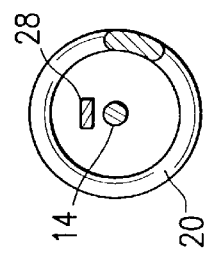
FIG. 3
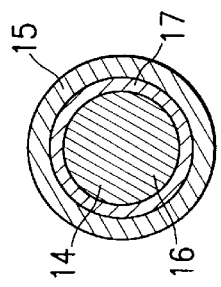
FIG. 2
FIG. 1

GUIDEWIRE HAVING SUBSTANTIALLY NICKEL-FREE HIGH-NITROGEN AUSTENITIC STAINLESS STEEL ALLOY

BACKGROUND

Metallic wires are widely used in medical procedures, a common example being the guidewires used to locate intravascular devices such as angioplasty catheters. Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means can be provided on the proximal end of the core member to rotate, and thereby steer, the guidewire while it is being advanced through a patient's vascular system.

A major requirement for guidewires and other guiding members, whether comprising solid wire or tubular members, is that they have sufficient column strength to be pushed through a patient's vascular system or other body lumens without kinking. However, they must also be flexible enough to avoid damaging the blood vessel or other body lumen through which they are advanced. Commonly, guidewires are formed from two or more materials. A relatively short, distal section is configured to have superior handling characteristics and may be shaped to aid in selecting the desired branch of the vasculature. The relatively long proximal section, on the other hand, should have a high column strength and torquability as its primary characteristic. Accordingly, prior art guidewires have been made with stainless steel alloys such as 304V stainless steel which can have a composition which includes about 10% nickel. Such alloys can also be used for the entire length of the guidewire. Although widely used, some stainless steel alloys suffer from being relatively brittle and are subject to fatigue. In addition, the nickel content can be a drawback for patients who are sensitive to this element.

Accordingly, there is a need for guidewire materials having high tensile strength, while maintaining good ductility, fracture toughness and high number of fatigue cycles and strength. It can also be desireable to have a guidewire material with a low nickel content.

SUMMARY

The invention is directed to an elongated intracorporeal member, specifically an elongated guiding member comprising a core member formed from a substantially nickel-free high-nitrogen austenitic stainless steel alloy. Such an alloy can have improved tensile and fatigue strength compared to conventional nickel-containing alloys and improved ductility and fatigue strength as compared to conventional high tensile strength alloys. As used herein, the term high nitrogen substantially nickel-free austenitic stainless steel alloy refers to an alloy which can have a nitrogen content of about 0.90 to about 0.99 weight percent, specifically, about 0.96 to about 0.98 weight percent. Such an alloy can have a nickel content of up to about 0.4 weight percent, specifically, up to about 0.3 weight percent and more specifically up to about 0.2 weight percent. The invention is also directed to a guidewire having a shapeable member at a distal end formed from the substantially nickel-free high-nitrogen austenitic stainless steel alloy.

BRIEF DESCRIPTION OF THE DRAWINGS

FIG. 1 is an elevational view, partially in section, of a guidewire having features of the invention.

FIG. 2 is a transverse cross sectional view of the guidewire of FIG. 1 taken along lines 2—2 in FIG. 1.

FIG. 3 is a transverse cross sectional view of the guidewire of FIG. 1 taken along lines 3—3 in FIG. 1.

DETAILED DESCRIPTION

FIGS. 1–3 illustrate a guidewire 10 embodying features of the invention configured to be inserted into a patient's body lumen, such as an artery. The guidewire 10 comprises an elongated, proximal portion 12 having a distal end 13 and being formed from substantially nickel-free high-nitrogen austenitic stainless steel alloy, a relatively short distal portion 14, and a connector element 15 that secures a proximal end 16 of the distal portion 14 to the distal end 13 of the proximal portion 12 in a torque transmitting relationship. The connector element 15 can be secured to the proximal end 16 and the distal end 13 with solder 17 or any other suitable material or method. The distal portion 14 has at least one tapered section 18 that becomes smaller in the distal direction. Helical coil 20 is disposed about the distal portion 14 and has a rounded plug 22 on the distal end thereof. The coil 20 is secured to the distal portion 14 at proximal location 24 and at intermediate location 26 by a suitable solder. A shaping ribbon 28 is secured by its proximal end 24 to the distal portion 14 at location 26 by the solder at location 26. A distal end 25 of the shaping ribbon 28 is secured to the rounded plug 22 which is usually formed by soldering or welding the distal end of the coil 20 to the distal end 25 of the shaping ribbon 28. A portion of helical coil 20 can be made of radiopaque metal such as gold, tantalum, platinum, platinum-nickel alloys or the like to facilitate fluoroscopic observation while disposed within a patient's body.

Distal portion 14 is typically formed from a material configured to impart desirable handling properties to guidewire 10. For example, pseudo- or super-elastic alloys and shape memory alloys, such as nickel-titanium alloys (Nitinol in particular), can be used to form distal portion 14. Other suitable materials can also be used to form either the proximal portion 12 or distal portion 14 including stainless steels such as 316L, 304, 304V, high tensile stainless steel, and precipitation handenable stainless steel. Other suitable materials include cobalt based MP35N and L605, and Elgiloy. Alternatively, proximal portion 12 and distal portion 14 both may be made from high-nitrogen substantially nickel-free austenitic stainless steel alloy without the need for connector 16.

In another embodiment of the invention, shaping ribbon 28 is formed from high-nitrogen substantially nickel-free austenitic stainless steel alloy. In such embodiments, proximal portion 12 and distal portion 14 may be formed from conventional materials, or high-nitrogen substantially nickel-free austenitic stainless steel alloy. In one embodiment, the entire core of guidewire 10, including proximal portion 12, distal portion 14 and shaping ribbon 28 are all a continuous piece of high-nitrogen substantially nickel-free austenitic stainless steel alloy.

The elongated proximal portion 12 of the guidewire 10 can be up to 300 cm in length, specifically about 150 to about 180 cm in length with an outer diameter of about 0.006 to 0.018 inch for coronary use. Larger diameter guidewires (e.g., up to 0.035 inch or larger) may be employed in peripheral arteries and other body lumens. The lengths of the smaller diameter and tapered sections can range from about 2 to about 20 cm, depending upon the stiffness or flexibility desired in the final product. The helical coil 20 is about 20 to about 45 cm in length, has an outer diameter about the same size as the diameter of the elongated proximal portion 12, and is made from wire about 0.002 to 0.003 inch in diameter. The shaping ribbon 28 can have a rectangular transverse cross-section, usually having dimensions of about 0.001 by 0.003 inch.

Suitable high-nitrogen substantially nickel-free austenitic stainless steel alloys used in this invention may be obtained from Carpenter Technology Corporation, Reading, Pennsylvania as BioDur® 108. An analysis of an embodiment of a high-nitrogen substantially nickel-free austenitic stainless steel alloy having features of the invention is:

| Element | Wt % |
|---|---|
| Carbon | up to 0.08 |
| Manganese | 23 +/- 3 |
| Silicon | up to 0.75 |
| Phosphorus | up to 0.03 |
| Sulfur | up to 0.01 |
| Chromium | 21 +/- 3 |
| Nickel | up to 0.3 |
| Molybdenum | 0.7 |
| Copper | up to 0.25 |
| Nitrogen | 0.97 +/- 0.02 |
| Iron | Balance |

As used herein, the term substantially nickel-free with regard to a stainless steel alloy means stainless steel alloys having up to about 0.4 weight % nickel, specifically, up to about 0.3 weight % nickel, and more specifically up to about 0.2 weight % nickel. The term high-nitrogen as used herein with regard to stainless steel alloys means a nitrogen content of about 0.90 to about 0.99 weight %, specifically about 0.96 to about 0.98 weight %.

The composition of an embodiment of a high-nitrogen substantially nickel-free stainless steel alloy can be up to 0.08 weight % carbon, about 20 to about 26 weight % manganese, up to about 0.75 weight % silicon, up to about 0.03 weight % phosphorous, up to about 0.01 weight % sulfur, about 18 to about 24 weight % chromium, up to about 0.4 weight % nickel, about 0.6 to about 0.8 weight % molybdanum, up to about 0.25 weight % copper and about 0.96 to about 0.98 weight % nitrogen with the balance consisting of iron. Yet another embodiment of a high-nitrogen substantially nickel-free stainless steel alloy can have a weight % composition of about 0.049 carbon, about 23.03 manganese, about 0.26 silicone, about 0.002 sulfur, about 21.17 chromium, about 0.23 nickel, about 0.7 molybdenum, about 0.01 copper, about 0.9 nitrogen, about 0.012 phosphorous, about 0.007 aluminum, about 0.02 cobalt, less than about 0.01 columbium, about 0.03 vadium, about 0.0029 boron and the balance iron.

At physiological temperatures, an embodiment of a high-nitrogen substantially nickel free stainless steel alloy having features of the invention can sustain impact energies up to about 136 J at 38° C and about 122 J at 22° C. before experiencing ductile rupture as tested by ASTM E23. Due to the austenitic nature of the embodiment, fatigue limit is closely related to tensile strength:

| Test Stress | | | Cycles to Fracture |
|---|---|---|---|
| (MPa) | (ksi) | (% UTS) | (×1000) |
| 517 | 75 | 56 | 40 |
| 448 | 65 | 48 | 37 |
| 414 | 60 | 44 | 224 |
| 396 | 57.5 | 43 | 612 |
| 379 | 55 | 41 | 23,512 |

The above data represent annealed alloy specimens of the embodiment with a grain size of ASTM #5 with an ultimate tensile strength (UTS) of 930 Mpa (135 ksi). The data show that the embodiment has a fatigue limit of about 14% of the tensile strength. The embodiment also exhibits superior resestande to pitting and crevice corrosion and is highly biocompatible. Finally, the embodiment can be non-magnetic and essentially free of ferrite phase.

Another useful parameter which can be measured on metal alloys is the endurance limit. Endurance limit is defined herein as the limit of cyclic stress that a material can withstand for an infinite number of loading cycles. Typically, a physical number of cycles actually used for testing is set at 1,000,000 cycles. One embodiment of a high-nitrogen substantially nickel-free stainless steel alloy as described herein can have an endurance limit of about 35 to about 52 ksi.

Described herein are preferred embodiments, however, one skilled in the art that pertains to the present invention will understand that there are equivalent alternative embodiments.

What is claimed is:

1. An elongated guiding member comprising a core member formed from high-nitrogen substantially nickel-free austenitic stainless steel alloy.

2. The elongated guiding member of claim 1, wherein the alloy comprises up to about 0.4 weight % nickel.

3. The elongated guiding member of claim 2, wherein the alloy comprises up to about 0.2 weight % nickel.

4. The elongated guiding member of claim 1, wherein the alloy comprises about 0.90 to about 0.99 weight % nitrogen.

5. The elongated guiding member of claim 1, further comprising a distal portion formed of a material having different handling characteristics than the high-nitrogen substantially nickel-free austenitic stainless steel alloy.

6. The elongated guiding member of claim 5, wherein the distal portion is formed from a nickel-titanium alloy.

7. The elongated guiding member of claim 1, further comprising a shapeable member at a distal end of the guiding member, wherein the shapeable member is formed from high-nitrogen substantially nickel-free austenitic stainless steel alloy.

8. An elongated guiding member comprising a shapeable memeber at a distal end of the guiding member, wherein the shapeable member is formed from high-nitrogen substantially nickel-free austenitic stainless steel alloy.

9. The elongated guiding member of claim 8, wherein the alloy comprises up to about 0.4 weight % nickel.

10. The elongated guiding member of claim 8, wherein the alloy comprises up to about 0.2 weight % nickel.

11. The elongated guiding member of claim 8, wherein the alloy comprises about 0.90 to about 0.99 weight % nitrogen.

12. The elongated guiding member of claim 8, further comprising an elongated proximal core member formed from high-nitrogen substantially nickel-free austenitic stainless steel alloy.

* * * * *